(12) United States Patent
Goodwin et al.

(10) Patent No.: US 7,733,490 B2
(45) Date of Patent: Jun. 8, 2010

(54) APPARATUS AND METHODS TO ANALYZE DOWNHOLE FLUIDS USING IONIZED FLUID SAMPLES

(75) Inventors: Anthony Goodwin, Sugar Land, TX (US); Oliver C. Mullins, Ridgefield, CT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 78 days.

(21) Appl. No.: 12/246,107

(22) Filed: Oct. 6, 2008

(65) Prior Publication Data

US 2009/0128818 A1    May 21, 2009

Related U.S. Application Data

(60) Provisional application No. 60/988,703, filed on Nov. 16, 2007.

(51) Int. Cl.
*G01N 21/00* (2006.01)
(52) U.S. Cl. .............. 356/436; 356/241.1; 356/70; 166/250.01; 250/269.1; 73/152.11
(58) Field of Classification Search ......... 356/432–440, 356/73, 70, 241.1; 166/250.01, 66; 250/269.1, 250/255, 256; 73/152.11, 152.55; 702/11
See application file for complete search history.

(56) References Cited

U.S. PATENT DOCUMENTS

| 5,902,939 | A | 5/1999 | Ballard et al. | |
|---|---|---|---|---|
| 7,084,392 | B2* | 8/2006 | DiFoggio et al. | 250/269.1 |
| 2004/0000636 | A1 | 1/2004 | Mullins et al. | |
| 2004/0045706 | A1* | 3/2004 | Pop et al. | 166/250.07 |
| 2006/0243047 | A1* | 11/2006 | Terabayashi et al. | 73/152.55 |
| 2007/0068242 | A1 | 3/2007 | DiFoggio | |
| 2007/0143023 | A1 | 6/2007 | Betancourt et al. | |
| 2009/0126928 | A1* | 5/2009 | Sumrall et al. | 166/250.01 |

FOREIGN PATENT DOCUMENTS

| WO | WO01/20322 | 3/2001 |
|---|---|---|
| WO | WO01/73424 | 10/2001 |
| WO | WO2005/017316 | 2/2005 |

* cited by examiner

*Primary Examiner*—Hoa Q Pham
(74) *Attorney, Agent, or Firm*—Dave R. Hofman

(57) ABSTRACT

Apparatus and methods to analyze downhole fluids are described herein. A disclosed example method involves obtaining a sample of a downhole fluid, and depressurizing at least a portion of the sample. Additionally, a disclosed example method involves ionizing at least the portion of the sample, and analyzing the ionized portion of the sample to determine a parameter of the downhole fluid.

30 Claims, 10 Drawing Sheets

US 7,733,490 B2

APPARATUS AND METHODS TO ANALYZE DOWNHOLE FLUIDS USING IONIZED FLUID SAMPLES

CROSS-REFERENCE TO RELATED APPLICATIONS

This patent application claims priority to U.S. Provisional Patent Application No. 60/988,703, filed on Nov. 16, 2007, which is hereby incorporated herein by reference in its entirety. This patent application is also related to U.S. patent application Ser. No. 12/246,039, entitled "APPARATUS AND METHODS TO ANALYZE DOWNHOLE FLUIDS USING IONIZED FLUID SAMPLES," filed concurrently herewith.

BACKGROUND OF THE DISCLOSURE

Drilling, completion, and production of reservoir wells involve measuring various subsurface formation parameters. Companies often measure percentages of oil, water, and gas mixtures contained in representative fluid samples drawn from wells to determine fluid composition or fluid quality. A detailed description of the fluid properties and characteristics is desirable for an accurate modeling of the fluids in the reservoir and to determine the economic value of producing hydrocarbons from the reservoir well.

Historically, the fluid samples were brought to the surface for analysis in a laboratory, but recent developments have facilitated directly measuring fluid properties downhole during a pumping or sampling sequence using downhole fluid analysis (DFA) techniques. In contrast to laboratory analyses or surface wellsite analyses, which may require a relatively extended amount of time to produce results and may result in undesirable phase transitions as well as the loss of key constituents in samples, DFA techniques may be used to perform fluid analysis in situ and to provide analysis results in real-time.

Known techniques for determining characteristics of a formation fluid often involve performing spectroscopic analysis at a particular wavelength to measure an optical response of the formation fluid that is indicative of the presence of a particular molecule. Additionally, known techniques for determining the characteristics of a formation fluid often involve performing a resistivity analysis of the formation fluid to facilitate a determination of composition of the formation fluid. However, known fluid analysis techniques typically target a limited of analytes, such as methane, carbon dioxide, water, or groups of analytes, such as alkanes having six or more carbon atoms in the molecule.

SUMMARY OF THE DISCLOSURE

In accordance with a disclosed example, an example method to analyze a downhole fluid involves conveying a testing tool in a wellbore, the testing tool having an inlet, a depressurizer, an ionizer, and a fluid measurement unit and obtaining a sample of the downhole fluid via the inlet. Additionally, the example method involves depressurizing at least a portion of the sample via the depressurizer, measuring a depressurizing pressure of the at least portion of the sample, ionizing the at least portion of the sample via the ionizer, and performing an analysis of the ionized portion of the sample. A parameter of the downhole fluid is determined from the measured depressurizing pressure and the analysis of the ionized portion of the sample.

In accordance with another disclosed example, an example apparatus to analyze a downhole fluid includes a testing tool adapted for conveyance in a wellbore, the testing tool comprising an inlet for obtaining a sample of the downhole fluid, a depressurizer to depressurize at least a portion of the sample, and an ionizer to ionize the at least the portion of the sample, and a fluid measurement unit to measure a characteristic of the ionized portion of the sample. Additionally, the example apparatus includes a processing unit configured to determine a parameter of the downhole fluid based on the characteristic of the ionized portion of the sample and a depressurizing pressure of the at least the portion of the sample.

DETAILED DESCRIPTION

Figure 1:
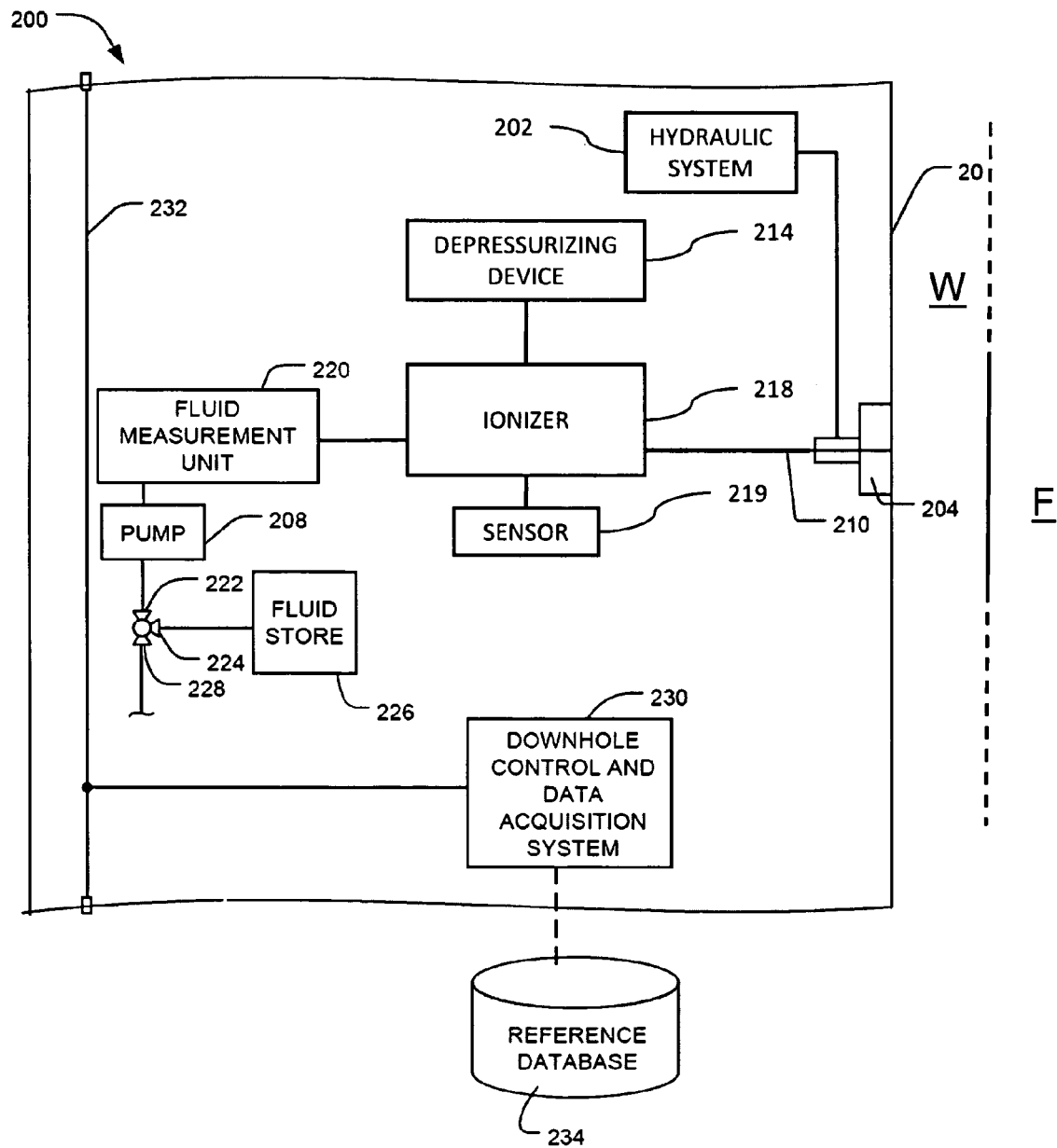
FIG. 1 depicts a block diagram of an example downhole tool that may be used to analyze formation fluid samples using ionized fluid samples.

Certain examples are shown in the above-identified figures and described in detail below. In describing these examples, like or identical reference numbers are used to identify common or similar elements. The figures are not necessarily to scale and certain features and certain views of the figures may be shown exaggerated in scale or in schematic for clarity and/or conciseness.

The example methods and apparatus described herein can be used to analyze fluids from a subsurface formation or a wellbore using fluid ionizing techniques. In particular, the example methods and apparatus described herein to analyze downhole fluids involve obtaining a fluid sample, depressurizing the sample (e.g., to convert a portion of the sample to a gaseous phase or to decrease the density or pressure of the fluid sample), ionizing the sample (e.g., to create a plasma, etc.), and analyzing the ionized fluid sample downhole. In the illustrated examples described herein, fluid samples can be ionized by moving the samples through an ionization chamber and exposing the samples to an ionizing energy such as, for example, an electrical charge, photons, or a lightwave emission, etc. The analyses described herein may be performed substantially downhole, partially downhole and partially uphole (i.e., at ground level), or entirely uphole (e.g., at a wellsite, in a laboratory, etc.).

The example methods and apparatus described herein can be used to ionize a depressurized sample (e.g. to create a plasma) by electrically charging atoms in the fluid samples to excite the atoms and cause the atoms to emit photons having wavelengths indicative of the presence of particular fluid components or molecules. In other words, the fluid samples can be ionized by applying an electrical field or charge to the fluid samples (e.g., bombarding the samples with electrons) to excite the atoms and cause the atoms to emit photons having respective wavelengths as the atoms return to their lower energy levels (i.e., their energy levels prior to the excitement). The wavelengths of the photons can be measured using a spectrometer to determine the presence of particular atoms corresponding to those wavelengths. Fluid analysis techniques such as, for example, spectrometer analysis techniques can be used to accurately identify atoms, molecules, substances, or fluid components (e.g., mercury, nickel, vanadium, sulfur, radon, polonium, barium, strontium, nitrogen, calcium, oxygen, helium, methane, ethane, propane, etc.) in fluid samples and the concentrations of those atoms, molecules, substances, or fluid components and/or atomic concentrations. The light intensities of the emitted wavelengths can be measured to determine the concentrations of those atoms. In addition to determining atomic concentration(s), detecting the presence of a particular atom in a fluid sample can be indicative of the presence of a particular molecule. For example, detecting the presence and concentration of sulfur (S) atoms can be indicative of the presence and concentration of hydrogen sulfide ($H_2S$) in a fluid sample. In addition, detecting the presence and concentration of sulfur (S) atoms can be or other thiols (mercaptans, hydrosulfides and thiolates, mercaptides) that are sufficiently volatile to vaporize into the gaseous portion of the depressurized sample.

The example methods and apparatus described herein can also be used to analyze a depressurized sample by measuring the resistivity of the fluid samples while or after emitting photons onto the samples (e.g., bombarding the samples with photons). Specifically, an ionizing photon source can be used to emit photons having a particular wavelength into a fluid sample. The fluid sample becomes ionized (e.g. to create a plasma) which, in turn, causes its resistivity characteristic to change based on its fluid component or molecular composition. Using a resistivity measurement device (e.g., an ohmmeter), the resistivity of the ionized sample can be measured, and a concentration of one or more analyte(s) can be determined based on the measured resistivity value and the particular photon wavelength and/or photon energy intensity used to ionize the fluid sample.

FIG. 1 depicts a block diagram of a downhole tool 200 that may be used to analyze formation fluid samples using ionized fluid samples. The downhole tool 200 that may be deployed in a wellbore W penetrating a subterranean formation F. In the illustrated example of FIG. 1, lines shown connecting blocks represent fluid and/or electrical connections that may comprise one or more flowlines (e.g., hydraulic fluid flowlines or formation fluid flowlines) or one or more wire or conductive paths. As shown in FIG. 1, the downhole tool 200 includes a hydraulic system 202 that may be fluidly coupled to a sampling probe 204 to extend the sampling probe 204 into engagement with the subterranean formation F to enable drawing formation fluid samples via the sampling probe 204. Additionally, the hydraulic system 202 may retract the sampling probe 204 toward or into a chassis or body 206 when the sampling operation is complete. However, the downhole tool 200 may also be used to analyze fluid samples from the wellbore W, in which case, an extendable probe may not be needed.

To draw a fluid (e.g., a formation fluid from the subterranean formation F or a wellbore fluid from the wellbore W) through a sample flowline 210, the downhole tool 200 is provided with a pump 208. In particular, the pump 208 draws fluid through the flowline 210, an ionizer 218, and a fluid measurement unit 220. In other example implementations, the ionizer, 218 and/or the fluid measurement 220 may be positioned along a bypass line (not shown). In the illustrated example, the ionizer 218 is implemented in connection with a depressurizing device 214 and a sensor 219, as described below in connection with FIGS. 2A and 2B. However, in other example implementations, the depressurizing device 214, the ionizer 218, and the sensor 219 may be in a serial arrangement connected by a flowline. To store or discard formation fluid samples, the pump 208 moves the fluid away from the flow line 210 to a valve 222, which has a first selectable outlet 224 that is fluidly coupled to a fluid store 226 and a second selectable outlet 228 that expels fluid out of the downhole tool 200 into the wellbore W for example.

The fluid measurement unit 220 may be used to determine properties of a fluid sample. The fluid measurement unit 220 may be provided with one or more other types of suitable sensors, for example, a nuclear magnetic resonance (NMR) sensor, a density sensor, a capacitance sensor, a viscosity sensor, a volumetric flowrate sensor, a resistivity measurement unit (an ohmmeter), an optical spectrometer, etc . . . to measure fluid characteristics (e.g. composition data). The properties measured with the fluid measurement unit 220 may be used for example to monitor formation fluid sample contamination by mud filtrate and to determine when the extract formation fluid has a sufficiently low contamination level for the depressurizing device 214, the ionizer 218 and the sensor 219 to be activated. Further, the properties measured with the fluid measurement unit 220 may also be used to determine the type of fluid being sampled. The fluid type data (e.g. composition data) can be used in conjunction with data provided by the sensor 219 to determine concentration levels of one or more analyte(s) in the fluid sample.

To convert at least a portion of the downhole fluid samples from a liquid state to a gaseous state and/or to decrease the pressure or density of an extracted formation fluid, the downhole tool 200 is provided with a depressurizing device 214. When formation fluid is drawn from the formation F or the wellbore W, it is typically in a liquid state having a relatively large density. The probability of ionizing a sample and the ionizing products not immediately reforming to the same molecule may be reduced in proportion to the sample density. Thus, the power required to ionize a high density fluid sample (e.g., a liquid) is usually relatively higher than the power required to ionize a low density sample (e.g., a gas). Due to the limited availability of power in a downhole tool, the depressurizing device 214 can be advantageously used to convert at least a portion of the downhole fluid samples into a gaseous phase to facilitate ionizing the fluid using relatively less electrical power. Alternatively, the depressurizing device 214 can be advantageously used to decrease the density of a formation fluid sample already in a gaseous state to facilitate ionizing the fluid using relatively less electrical power. For example, the depressurizing device 214 can depressurize the fluid sample or a portion thereof to induce phase separation.

Alternatively, the fluid may be depressurized using the pump 208 by closing a valve (for example the valve 1008 in FIGS. 2A and 2B) on the flowline 210 and reducing the pressure in an isolated portion of the flow line 210.

To ionize fluid samples, the downhole tool 200 is provided with the ionizer 218. In some example implementations, the ionizer 218 ionizes the sample by exposing the sample to, for example, an electrical field or charge, photons, lightwaves, etc. for a particular duration at a particular energy level to change at least a portion of the sample to a plasma that can be measured using a sensor 219. The ionizing power delivered by the ionizer should be greater than the minimum required for ionization of the gaseous portion of the depressurized sample. The ionizing duration is the amount of time for which a formation fluid sample is exposed to a source of ionizing radiation and the energy level is an energy level sufficiently high enough to cause the fluid sample to be sufficiently ionized to obtain fluid measurement values that can be used to determine a concentration of an analyte. In the illustrated examples, the sensor 219 is coupled to the depressurizing device 214 to measure a characteristic of the plasma generated by the ionizer 218.

To measure the fluid samples after being ionized, the downhole tool 200 is provided with the sensor 219. For example, if the sensor 219 is to measure resistivity characteristic changes in fluid samples before and/or after ionization, the sensor 219 can be provided with resistivity measurement units (e.g., ohmmeters). Alternatively, if the sensor 219 is to measure spectroscopic characteristics of fluid samples, the sensor 219 can be implemented using one or more spectrometers configured to measure a single wavelength (e.g., a wavelength parameter) or a plurality of wavelengths (e.g., a plurality of wavelength parameters). That is, if a fluid is analyzed to identify the presence and concentration of only a single type of molecule (e.g., a hydrogen sulfide ($H_2S$) molecule) in fluid samples, the spectrometer(s) of the fluid measurement unit 220 can be configured to measure a wavelength corresponding to an atom (e.g., a sulfur (S) atom) present in the molecule of interest. Alternatively, if a fluid is analyzed to identify the presence and concentration of a plurality of molecules in fluid samples, the spectrometer(s) of the sensor 219 can be configured to measure a plurality of wavelengths corresponding to atoms (e.g., sulfur (S) atoms, mercury atoms, nickel atoms, etc.) present in those molecules of interest. In any case, the parameter measurement values obtained using the sensor 219 may be used to identify particular atoms or molecules present in fluid samples based on models for those atoms or molecules produced by the ionization process of the ionizer 218.

Figure 2A:
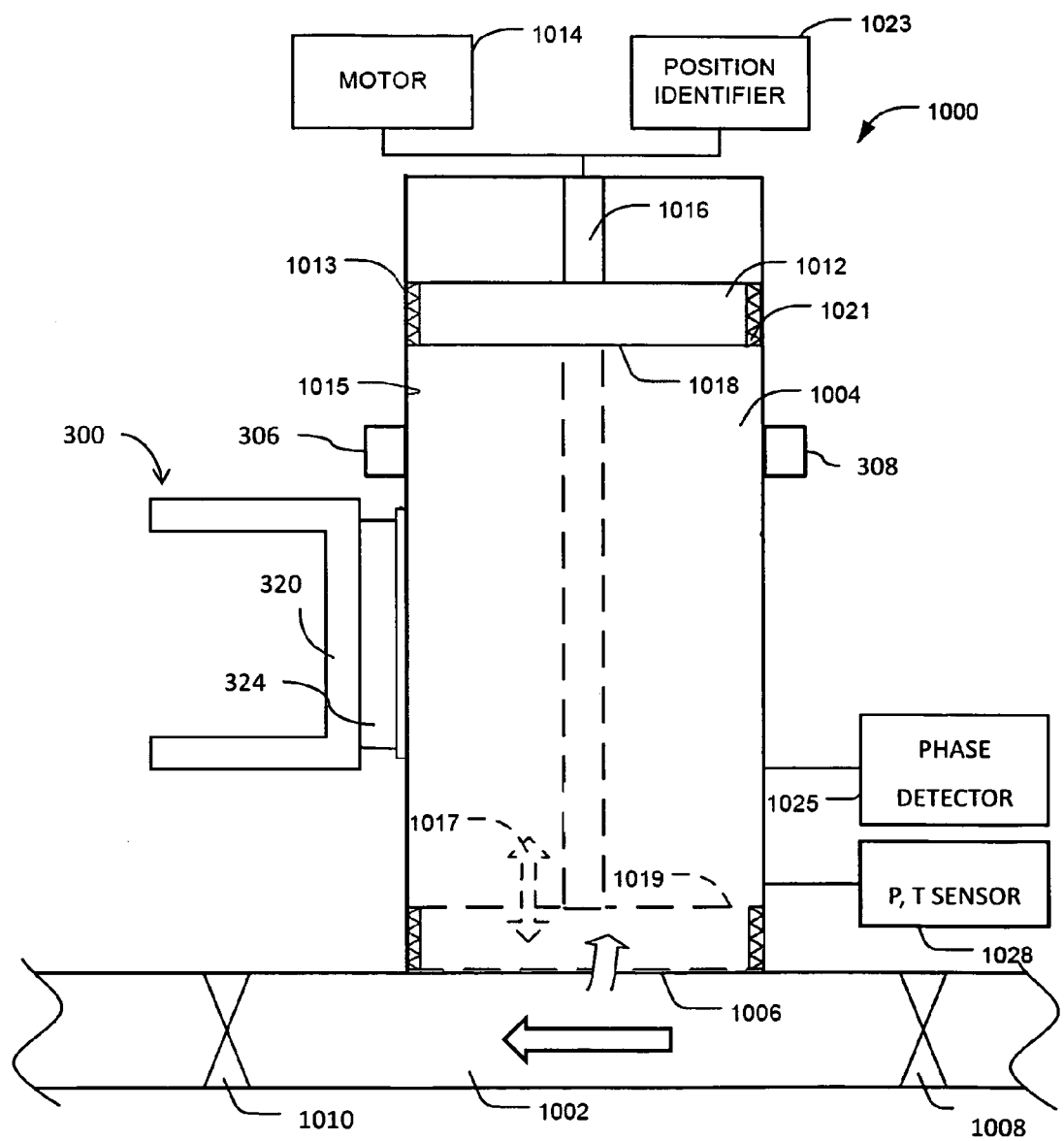
FIG. 2A depicts a block diagram of an example apparatus to analyze downhole fluids using ionized fluid samples that may be implemented in connection with the example downhole tool of FIG. 1.
Figure 2B:
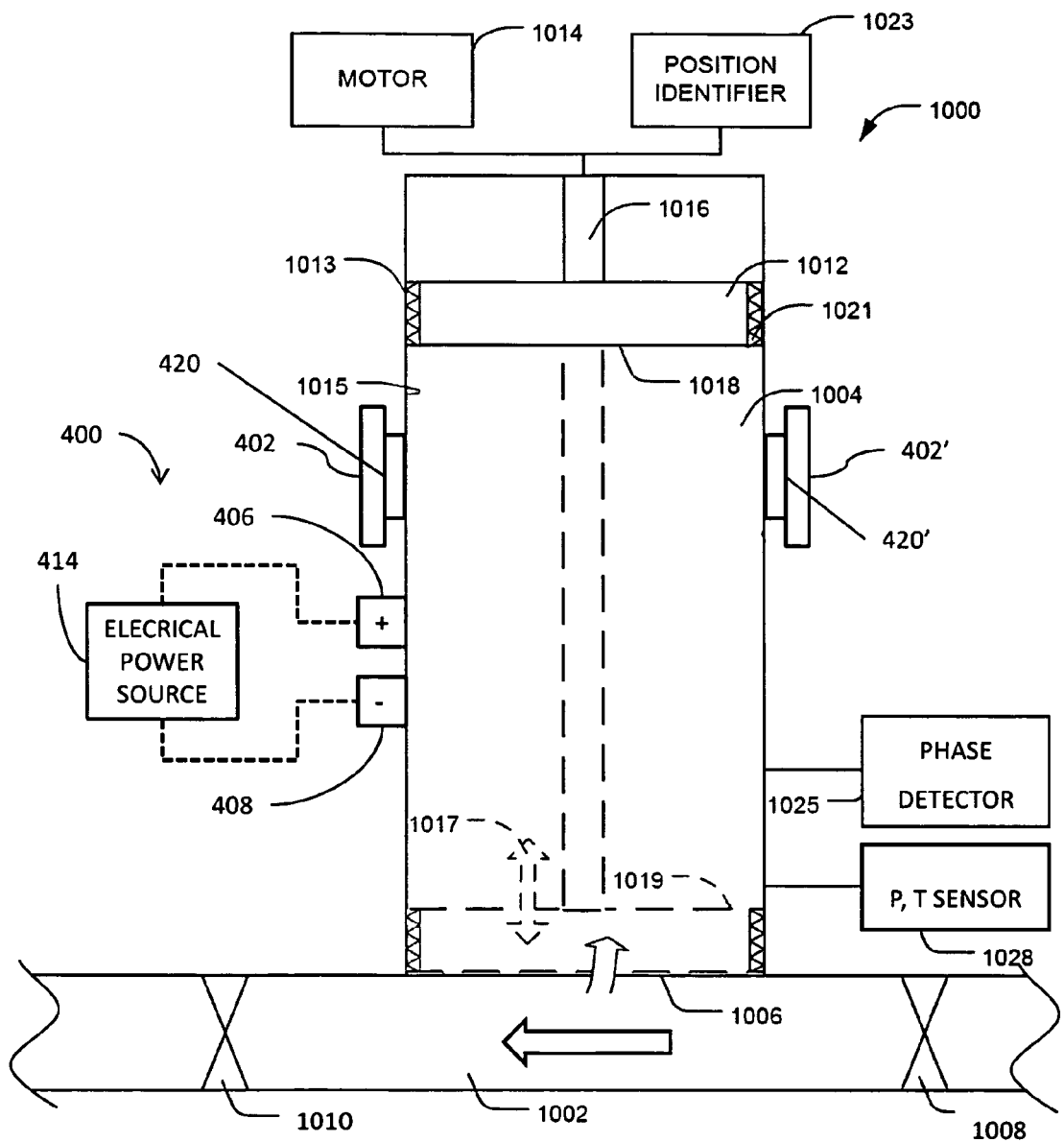
FIG. 2B depicts a block diagram of another example apparatus to analyze downhole fluids using ionized fluid samples that may be implemented in connection with the example downhole tool of FIG. 1.

In the illustrated examples, the sensor 219 may be implemented in connection with an optical spectrometer or a resistivity measurement unit, as further described in FIGS. 2A and 2B. However, in other example implementations, the sensor 219 may be implemented by any suitable plasma measurement unit. Further, although the downhole tool 200 is provided with one sensor 219, in other example implementations, any number of plasma sensors (e.g., 2, 3, etc.) may be used that may measure one or more parameters of the fluid sample after ionizing the fluid sample.

To control or collect data from the hydraulic system 202, the pump 208, the depressurizing device 214, the ionizer 218, the sensor 219, the fluid measurement unit 220, and the valve 222, the downhole tool 200 is provided with a downhole control and data acquisition system 230. Although not shown, the downhole control and data acquisition system 230 may include a processor, one or more memories, and a communication interface (e.g., a modem). The communication interface of the downhole control and data acquisition system 230 may be communicatively coupled to a surface system to communicate analysis data and/or receive control data. The wires or lines 232 may include a databus (e.g., carrying digital information and/or analog information), electrical power lines, etc. and may be implemented using a single conductor or multiple conductors.

Figure 6:
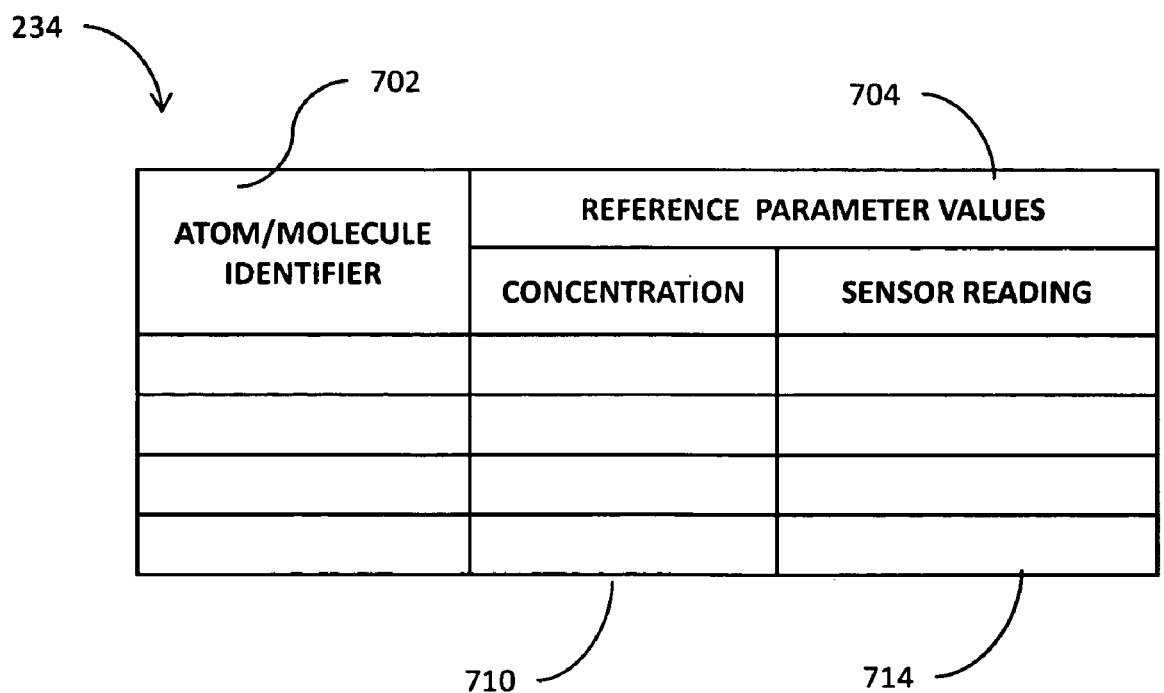
FIG. 6 is an example reference database that may be used to store reference measurement data of fluids having known fluid components and fluid component concentrations.

To store reference measurement values of reference formation fluids known to have particular fluid compositions, the downhole control and data acquisition system 230 may store or be communicatively coupled to a reference database 234. The reference measurement values can be used to identify fluid compositions of subsequently measured formation fluid samples. In some example implementations, the reference database 234 may be additionally or alternatively stored in a surface data acquisition surface. An example implementation of the reference database 234 is depicted in FIG. 6.

Turning now to FIGS. 2A and 2B, a detailed block diagram depicts an example apparatus 1000 to analyze downhole fluids using ionized fluid samples in a depressurized condition. The example apparatus 1000 may be used to implement the depressurizing device 214, the ionizer 218, and the sensor 219, of FIG. 1. The example apparatus 1000 includes a flowline 1002 that is fluidly coupled to the flowline 210 of FIG. 1, or a flowline (not shown) that bypasses the flowline 210 of FIG. 1. The flowline 1002 that is further fluidly coupled to a depressurizing chamber 1004 at an opening 1006 having a piston 1012 therein. Additionally, a first valve 1008 and a second valve 1010 are positioned within the flowline 1002 and may open or close to enable fluid to flow through the flowline 1002 or to retain at least a portion of the fluid between the first valve 1008 and the second valve 1010.

The depressurizing chamber 1004 and the piston 1012 may be used to implement the depressurizing device 214 of FIG. 2B. In the illustrated example, the piston 1012 is slidably movable within the depressurizing chamber 1004. An outer diameter surface 1013 of the piston 1012 is slidably and sealingly engaged to an inner diameter surface 1015 of the depressurizing chamber 1004 such that as the piston 1012 extends and retracts within the depressurizing chamber 1004 as indicated by arrow 1017, the piston 1012 changes the pressure within the depressurizing chamber 1004. The piston 1012 is operatively coupled to a motor 1014 via a rod 1016. The motor 1014 may be any suitable motor such as, for example, a stepper motor that moves the piston 1012 between, for example, a non-depressurized position (indicated by dashed lines 1019) and a depressurized position (in which the piston 1012 is shown in FIGS. 2A and 2B). In the non-depressurized position 1019, a surface 1018 of the piston 1012 is substantially in abutment with the flowline 1002 to decrease the volume containing a fluid sample. Additionally, the example apparatus 1000 may be provided with a position identifier 1023 that may be a Linear Variable Displacement Transducer (LVDT) or a counter to determine how far the piston 1012 moves or the position of the piston within the depressurizing chamber 1004. Specifically, the LVDT may measure the displacement of the piston 1012 and the counter may determine how far the piston 1012 moves by counting the number of revolutions that the motor 1014 has made.

In the illustrated example, the outer diameter surface 1013 of the piston 1012 is provided with a cleaning element 1021 (e.g., a squeegee structure) disposed between the outer diameter surface 1013 and the inner diameter surface 1015. In this manner, as the piston 1012 moves, the cleaning element 1021 can remove build-up or debris that may have accumulated on the inner diameter surface 1015 of the depressurizing chamber 1004 to facilitate performing measurements disposed thereon.

As shown, the example apparatus 1000 is positioned, such that, the flowline 1002 is located below the piston 1012 relative to the local acceleration of free-fall. Thus, relatively denser portions of a fluid sample will settle closer to the flowline 1002 and relatively less dense fluid will fill the depressurizing chamber 1004 closer to the surface 1018 of the piston 1012 because gravity will pull the relatively heavier fluid portion downward. In addition, the example apparatus 1000 may optionally be provided with a sample phase detector 1025 that may be used to determine the volume or the level at which a portion of the fluid that is in a liquid phase is positioned within the depressurizing chamber 1004. The sample phase detector 1025 may be implemented using any suitable apparatus such as, for example, an acoustic transducer, a plurality of LEDs, a plurality of resistors, or a video camera. Specifically, an acoustic transducer may identify the reflection between the gaseous phase and the liquid phase of the sample, the plurality of LEDs may be associated with identifying the difference in light attenuation between the liquid phase and the gaseous phase (e.g. an optical refraction index change), the plurality of resistors may be used to distinguish a water phase from a gaseous phase, and the video camera may be used to identify bubbles or particles within the sample that are associated with the presence of more than one phase.

In operation, the piston 1012 is initially in the non-depressurized position 1019 and the first valve 1008 and the second valve 1010 are in an open position. A sample of the downhole fluid flows through the flowline 1002 under the action of a pump (e.g. the pump 208 of FIG. 1). When sufficient clean or representative fluid is captured in the flowline 1002 between the first and second valves 1008 and 1010 (as determined for example using measurements performed with the fluid measurement unit 220 of FIG. 1), the first valve 1008 and the second valve 1010 are actuated to a closed position. Thus, as the fluid at relatively high pressure is captured between the first valve 1008, the second valve 1010 and the piston 1012.

The motor 1014 then incrementally moves the piston 1012 to the depressurized position, until a pressure of the sample fluid is reduced to a predetermined pressure and/or until the sample fluid comprises more than one phase (e.g., a liquid phase and a gaseous phase). As the piston 1012 moves toward the depressurized position, the sample fluid expands to substantially fill the depressurizing chamber 1004, thereby decreasing the pressure and/or the density of the sample fluid. In the illustrated example, moving the piston 1012 to the depressurized position increases a volume in the depressurizing chamber 1004 that the formation fluid may occupy by approximately ten times. In this manner, by decreasing the pressure of the sample fluid, the effect of spectral line broadening in optical measurements that may arise from interatomic interactions is substantially reduced.

Additionally, the example apparatus 1000 is provided with a sensor 1028 that may measure any suitable characteristic of the formation fluid such as, for example, the temperature, and the pressure of the sample fluid. The pressure and temperature data collected by the sensor 1028 may be used for example to determine whether a phase change has occurred during depressurization of the sample, as described thereafter in FIG. 4. For example once the sensor 1028 has determined that the formation fluid comprises more than one phase, the motor 1014 stops moving the piston 1012 and the position identifier 1023 identifies the position of the piston 1012 within the depressurizing chamber 1004 to determine to volume of the sample. The volume of the sample is determined by multiplying the distance between the opening 1006 and the surface 1018 of the piston 1012 by the radius of the depressurizing chamber 1004 squared by pi (e.g., $L*\Pi*r^2$), and adding the known volume of the flow line 1002 between the valves 1008 and 1010. The sample phase detector 1025 then identifies the level of the liquid phase of the sample to determine its volume. The volume of the liquid phase of the sample may be inferred or determined by subtracting volume of the gaseous phase of the sample from the total volume of the sample.

Once the volumes of the different phases are determined, a parameter(s) of the depressurized sample is measured, such as a resistivity value (as illustrated in FIG. 2A) or a light intensity value at one or more wavelengths (as illustrated in FIG. 2B). Regardless whether a resistivity value or a light intensity value is measured, the measured values are then compared to known measurements stored in the reference database 234. Specifically, the reference database 234 may contain a plurality of calibration measurements and/or data, which may have been obtained from subterranean formation fluids that have similar conditions having known analyte concentrations. By comparing these measured values of the gaseous phase with reference parameters stored in the database 234, the analyte concentration in the gas may be determined. Further, the analyte concentration in the downhole sample prior to depressurization can be inferred from data including one or more of the analyte concentration in the gas, the volume of the sample and/or the volume of the different phases of the sample, the pressure and temperature of the depressurized sample, and composition data provided for example by the fluid measurement unit 220.

After the sample is ionized and/or measurements are obtained from the sample, the piston 1012 is moved back to the non-depressurized position 1019, the first valve 1008 and the second valve 1010 are opened, and the sample flows through the flowline 1002 under the action of the pump 208 (FIG. 1) for example.

Referring now specifically to FIG. 2A, an example ionizer 300, which may be used to implement the ionizer 218 of FIG. 2B, is configured to ionize formation fluid samples by exposing the fluid samples to an ionizing source 320 that emits light waves and/or photons at a particular wavelength or range of wavelengths. The ionizing source 320 may be any suitable source such as, for example, a hot cathode mercury filled lamps or the like.

To ionize a fluid sample, the ionizing source 320 emits an ionizing radiation into the fluid sample in the chamber 1004 and the energy is absorbed by the fluid sample. In example implementations in which the ionizing source 320 is implemented using a photon emission source, as the photons are absorbed by a fluid sample, at least a portion of the fluid sample changes to a plasma state and the resistivity characteristics of the fluid samples change in ways that are indicative of the fluid components or molecular compositions of the fluid samples.

The chamber 1004, which can be provided with a resistivity meter (e.g., an ohmmeter having a first positive terminal 306 and a second negative terminal 308 abutting the chamber 104) to measure the resistivity parameter of the fluid sample after ionization. However, other resistivity meter may alternatively be used, such as an emitter coil or electro-magnetic antenna 306 and a receiver coil or electromagnetic antenna 308. The measured resistivity parameter of the fluid sample after ionization can be used to determine a concentration of one or more analyte.

In operation, after depressurizing the formation fluid, the ionizer 300 ionizes the sample by emitting an electromagnetic radiation (e.g. a visible or non visible light, X rays, gamma rays) in the sample for a particular duration at a particular energy level or wavelength to change at least a portion of the sample to a plasma (e.g., ionize the fluid sample). The energy level or wavelength is selected based on the types of the atoms (e.g. sulfur atoms, mercury atoms, nickel atoms, vanadium atoms, calcium atoms, oxygen atoms, helium atoms, etc.) targeted by the analysis, as further described in FIG. 5. The resistivity of the generated plasma (e.g. ionized sample) can be measured between the electrode 306 and 308. The plasma resistivity drop resulting from the fluid sample irradiation can be observed for a plurality of selected frequency or range of frequencies. The detection of a resistivity change resulting from the irradiation at different frequencies or wavelengths may indicate the presence of different species in the formation fluid. These resistivity measurements can be used along with a calibration table to determine a concentration of an element or elements present in the fluid sample, and then the species present in the formation fluid can be inferred or determined.

Specifically, during exposure to electromagnetic radiation at a particular wavelength characteristic of a particular atom or molecule, the electrons of these atoms or molecules are promoted a higher energy level by absorbing a photon at a particular wavelength characteristic of that atom (e.g., a photon wavelength characteristic of the type of atom such as, for example, a sulfur atom, a nickel atom, etc.). As this electronic transition occurs, these atoms or molecules get ionized. As the sample gets ionized, its resistivity decreases. Thus, the wavelengths at which the sample resistivity decreases are indicative of the presence and concentration of a particular species in the sample fluid.

The wavelengths emitted by the ionizing source 320 emits can be selected using a plurality of essentially mono-chromatic sources tuned to characteristic wavelength of one or more analytes of interest (e.g., sulfur atoms, mercury atoms, nickel atoms, vanadium atoms, calcium atoms, oxygen atoms, helium atoms, etc.) to identify the atoms present in the fluid sample. Alternatively, optical filters may be used to select the wavelengths transmitted to the fluid sample from a broad band light source. In addition, the resistivity levels of plasma generated by irradiating the sample can also be measured to determine the concentrations of the atoms or molecules present in the fluid sample. To determine the concentrations of atoms or molecules, a calibration table can be generated and stored in the reference database 234 to store reference intensity level measurements of reference fluids known to have particular atom or molecule concentrations in association with respective concentration values. In this manner, when a resistivity value corresponding to an emitted wavelength is measured, the resistivity value can be compared to resistivity value measurements in the calibration table to determine a concentration level of a detected atom or molecule.

Referring now specifically to FIG. 2B, another example ionizer 400 that may be used to implement the example ionizer 218 of FIG. 1 is depicted. The example ionizer 400 is configured to ionize fluid samples by applying an electric field or charge to the samples to bombard the samples with electrons, thereby generating a spark in the fluid samples. In the illustrated example, the ionizer 400 may include a positive terminal 406 (e.g., an anode), a negative terminal 408 (e.g., a cathode), and an electrical power source 414. Both positive and negative terminals are abutted to the chamber 1004. The electrical power source 414 is used to apply an electric field or charge to the fluid sample (e.g., apply a high voltage difference across the fluid sample) via the terminals 406 and 408 to increase the energy level of the molecules and/or atoms in the sample and to change at least a portion of the fluid sample to a plasma. This, in turn, may cause an avalanche effect in which electron charging propagates throughout the fluid sample causing atoms in the sample to transition to a higher energy level.

Additionally, the example apparatus 1000 is provided with a first spectrometer 402 and a second spectrometer 402' that are each provided with windows 420 and 420' (e.g., optical windows) that are substantially adjacent and/or flush with the inner diameter surface 1015 of the depressurizing chamber 1004. The windows 420 and 420' may be implemented using any suitable material such as, a sapphire material, a quartz material, and the like. The first and second spectrometers 402 and 402' may be implemented using any suitable spectrometers such as, for example, spectrometers capable of performing atomic emission spectroscopy measurements. In some examples, a diffraction grating spectrometer may be used to analyze substantially all of the species present in a formation fluid.

In operation, after depressurizing the formation fluid, the ionizer 400 ionizes the sample by inducing an electric field or charge through the sample for a particular duration at a particular energy level to change at least a portion of the sample to a plasma (e.g., ionize the fluid sample) that can be measured using the first and/or the second spectrometers 402 and 402'. A light intensity that is released from the formation fluid after ionization can be observed for a particular frequency or range of frequencies. These measurements can be used along with a calibration to determine a concentration of an element or elements present in the formation fluid, and then the species present in the formation fluid can be inferred or determined. This process is known as atomic emission spectroscopy. The presence of different frequencies or wavelengths may indicate the presence of different species in the formation fluid.

Specifically, during or after exposure to the electric field or charge, as each atom returns to a lower energy level it emits a photon at a particular wavelength characteristic of that atom (e.g., a photon wavelength indicative of the type of atom such as, for example, a sulfur atom, a nickel atom, etc.). A photon is produced when an electron falls to its normal electron orbit from a higher orbit to which it is displaced by the application of the electric field or charge by the ionizer 400. As the electron of an atom falls or returns from its excited, higher electron orbit to its normal electron orbit, the electron emits a photon having a specific wavelength corresponding to the type of the atom. Thus, the energy levels of the atoms decrease, thereby causing each of the atoms to emit photons at corresponding wavelengths.

The wavelengths can be measured by a spectrometer (e.g., the spectrometers 420 and 420') to determine the types of the atoms (e.g. sulfur atoms, mercury atoms, nickel atoms, vanadium atoms, calcium atoms, oxygen atoms, helium atoms, etc.) present in the fluid sample. In the example of FIG. 2B, the first and second spectrometers 402 and 402' may obtain optical measurements of the gaseous phase of the depressurized sample at some specific wavelengths indicative of particular analytes, as further described in FIG. 5. In addition to measuring the wavelengths of the photon emissions, the intensity levels of the emitted photon wavelengths can also be measured to determine the concentrations of the atoms or molecules present in the fluid sample. To determine the concentrations of atoms or molecules, a calibration table can be generated and stored in the reference database 234 to store reference intensity level measurements of reference fluids known to have particular atom or molecule concentrations in association with respective concentration values. In this manner, when an intensity level of an emitted wavelength is measured, the intensity level can be compared to intensity level measurements in the calibration table to determine a concentration level of a detected atom or molecule.

Figure 3:
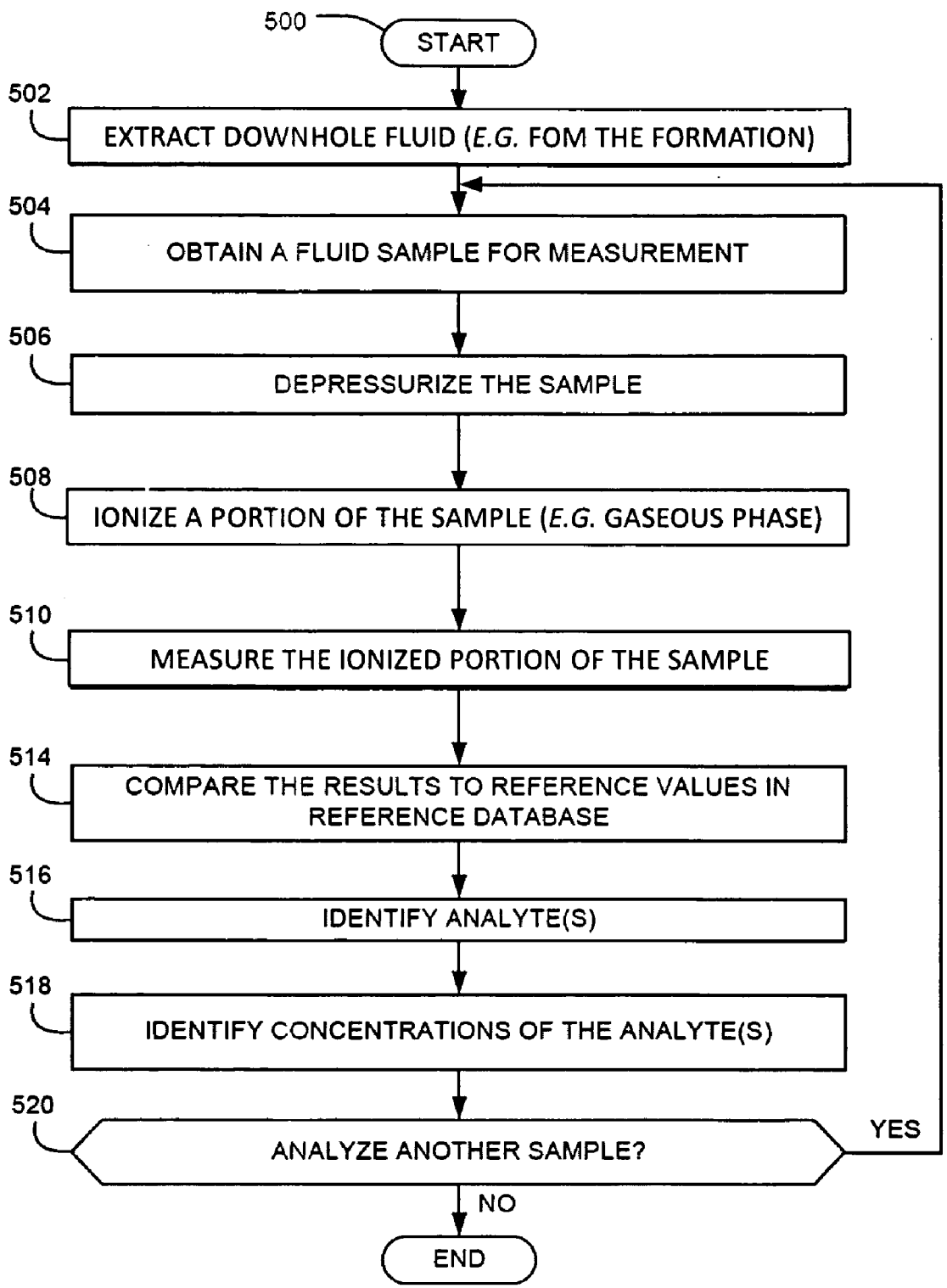
FIG. 3 is a flow diagram of an example method that may be used to identify fluid components and component concentrations in formation fluid samples.
Figure 4:
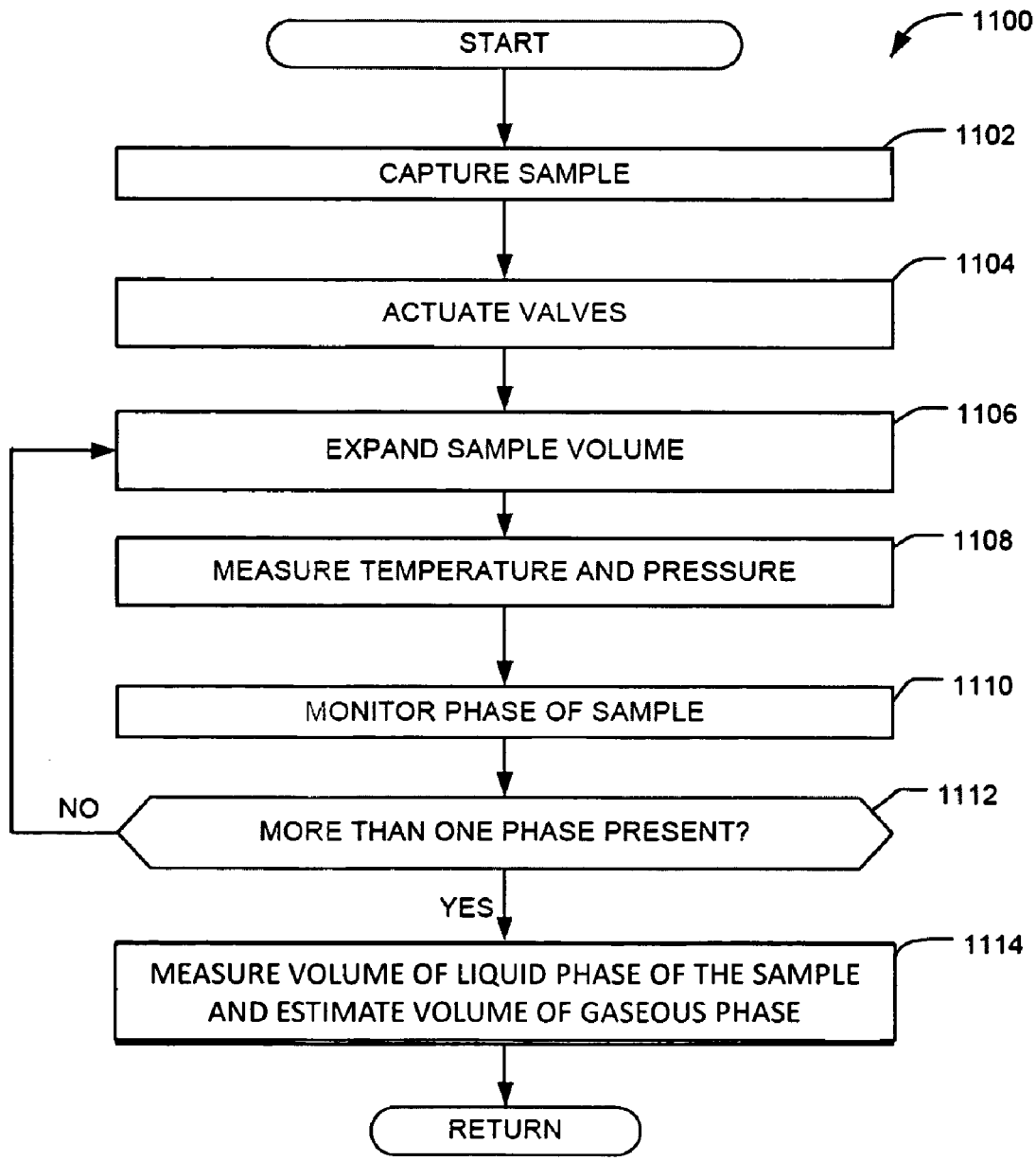
FIG. 4 is a flow diagram of an example method that may be used to perform formation fluid samples depressurization.
Figure 7:
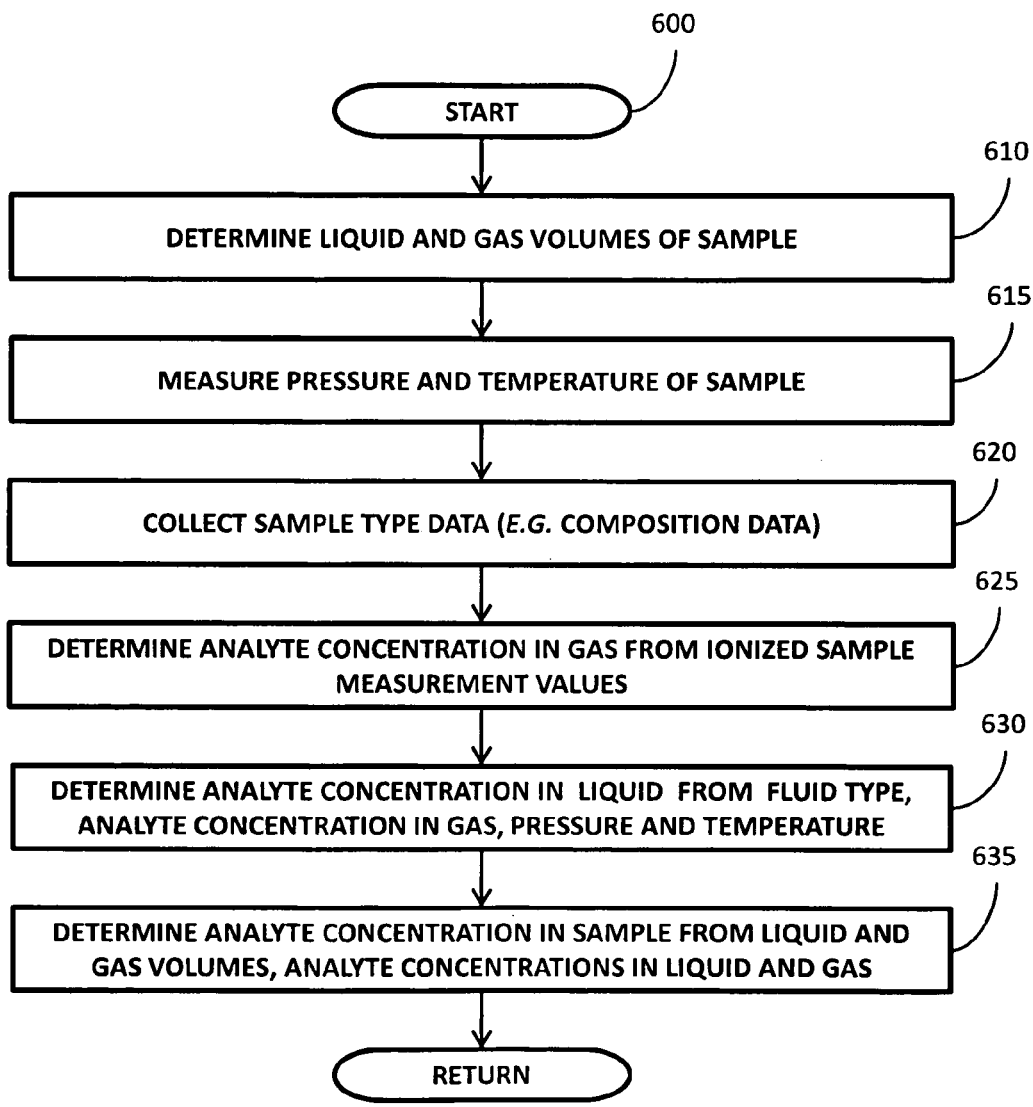
FIG. 7 is a flow diagram of an example method that may be used to determine analyte concentration in a fluid sample.

FIGS. 3, 4 and 7 are flowcharts of example methods that can be used to analyze fluid samples drawn from a subterranean formation (e.g., the formation F of FIG. 1) or from the wellbore (e.g., the wellbore W of FIG. 1). The example methods of FIGS. 3, 4 and 7 may be implemented in conjunction with the example downhole tool 200 of FIG. 1, and the example apparatus 1000 (FIGS. 2A and 2B). The example methods of FIGS. 3, 4 and 7 may be implemented using software and/or hardware. In some example implementations, the flowcharts can be representative of example machine readable instructions, and the example methods of the flowcharts may be implemented entirely or in part by executing the machine readable instructions. Such machine readable instructions may be executed by one or both of surface systems and/or the downhole control and data acquisition system 230 (FIG. 1). In particular, a processor or any other suitable device to execute machine readable instructions may retrieve such instructions from a memory device (e.g., a random access memory (RAM), a read only memory (ROM), etc.) and execute those instructions. In some example implementations, one or more of the operations depicted in the flowcharts of FIGS. 3, 4 and 7 may be implemented manually. Although the example methods are described with reference to the flowcharts of FIGS. 3, 4, and 7 persons of ordinary skill in the art will readily appreciate that other methods may additionally or alternatively be used in conjunction with the downhole tool 200, and/or the example apparatus 1000. For example, the order of execution of the blocks depicted in the flowcharts of FIGS. 3, 4 and 7 may be changed and/or some of the blocks described may be rearranged, eliminated, or combined.

FIG. 3 is a flow diagram depicting an example method 500 that may be used to draw and analyze formation fluid samples using, for example, the downhole tool 200 of FIG. 1. Initially, the sampling probe 204 (FIG. 1) extracts (e.g., admits, draws, etc.) downhole fluid, for example from the formation F or the wellbore W (block 502). In the cases the downhole fluid is extracted from the formation, the fluid measurement unit 220 (FIG. 1) may be used to determine a fluid property as the downhole fluid is drawn into the downhole tool 200. The value of the property is monitored while pumping and a contamination level of the fluid extracted from the formation by mud filtrate is determined using methods known in the art. When the contamination level is deemed sufficiently low to have a downhole fluid representative of the connate formation fluid in the ionizer 218, fluid extraction may stop. Regardless the type of downhole fluid (formation fluid or wellbore fluid) the ionizer 218 (FIG. 1) then obtains a formation fluid sample for measurement (block 504).

The depressurizing device 214 (FIG. 1) depressurizes the formation fluid sample (or a portion thereof) (block 506). In some example implementations, the pressure of the downhole fluid can be decreased to change at least a portion of the formation fluid to a different phase such as, for example, from a liquid phase to a gas phase. Alternatively, the pressure of a sample fluid that is already in a gaseous phase may be reduced to change at least a portion of the sample fluid to a relatively less dense gas. One example implementation of block 506 is described in further detail in FIG. 4.

The ionizer 218 ionizes the fluid sample (block 508) by, for example, exposing the sample to an electrical field, an ionizing radiation, photons, etc. for a particular amount of time at a particular energy level. The duration of exposure and the energy level used may be determined or selected based on experiments with similar samples to determine the amount of exposure and the energy level that may be needed to ionize the sample to, for example, change at least a portion of the fluid sample (e.g. a gaseous phase) to plasma. Preferably, the ionizer 218 emits sufficiently strong photon energies at a particular wavelength, or induce sufficient electrical discharge or spark in the portion of the fluid sample that all the analytes (e.g. atoms or molecules) targeted by the analysis are ionized. The example chart discussed below in connection with FIG. 5 may be used to implement the operations of block 508 to ionize the fluid sample.

The sensor 219 then measures the ionized portion of the fluid sample (block 510). For example, the sensor 219 may use spectroscopic measurements, resistivity measurements, etc.) as discussed above to collect wavelength or resistivity parameter measurement values that can be used to determine or identify a concentration of one or more analyte of the fluid sample. The downhole control and processing system 230 (FIG. 1) and/or a surface data acquisition system may be configured to store and/or process the measurement data corresponding to the ionized sample in a memory (e.g., a database).

In real time or during a post process, compare measurement values of the ionized sample to the reference measurements (of known fluid compositions) stored in the reference database 234 (block 514). The downhole control and data acquisition system 230 or a surface acquisition system identifies the analyte(s) (e.g., one or more elements) in a downhole fluid sample (block 516) based on the comparisons to the reference measurements in the reference database 234.

An example manner that may be used to identify the analyte(s) in a downhole fluid sample involves emitting ionizing light at predefined wavelengths that are associated with particular atoms or molecules and ionization with the ionizer 300 (FIG. 2A). Resistivity values of the ionized portion of fluid sample are measured by the electrodes or antennae 306 and 308 (FIG. 2A) after or during photon emission. The measured resistivity values are compared to resistivity values of the reference database 234. If, for a predefined wavelengths of photon emissions corresponding to particular atoms or molecules, the measured resistivity value exceed a threshold value stored in the reference measurements in the reference database 234, the downhole control and data acquisition system 230 or a surface acquisition system can determine that the measured formation fluid sample includes the said molecule or atom associated with predefined wavelengths of photon emissions in the reference database 234.

Another example manner that may be used to identify the analyte(s) in a downhole fluid sample involves comparing the photon wavelengths emitted by the formation ionized portion of fluid sample and measured by the spectrometer 402 and/or 402' (FIG. 2B) after electrical discharge and ionization with the ionizer 400 (FIG. 2B) to photon wavelengths of the reference database 234 that are associated with particular atoms or molecules. If the wavelengths of photon emissions corresponding to a formation fluid sample matches a particular wavelength of the photon emission of the reference measurements in the reference database 234, the downhole control and data acquisition system 230 or a surface acquisition system can determine that the measured formation fluid sample includes a molecule or atom stored in the reference database 234 in association with the matching reference measurement.

Further, the downhole control and data acquisition system 230 can infer the concentration of the molecule or atom in the ionized portion of the downhole fluid sample based on, for example, the measured resistivity value or the light intensity of the detected wavelengths. For example, the reference database 234 may store the measured resistivity values or the light intensities at predefined wavelengths for a plurality of known concentrations of analyte(s). The downhole control and data acquisition system 230 or a surface acquisition system can use a relationship (e.g. a calibration) between measured values by the sensor 219 and the analyte concentrations. Still further, the concentration of the molecule or atom in the depressurized sample may be used to identify the concentrations of the analyte(s) in the sample fluid in its pristine state in the formation, or before depressurization (block 518). For example, when the downhole fluid sample is a gas, the analyte concentration in the depressurized downhole fluid, together with the measured volumes of the non-depressurized and depressurized sample are used to compute the analyte concentration in the non-depressurized or pristine state downhole fluid. In other examples, when the downhole fluid sample undergoes a phase transition during depressurization, the analyte concentration in the ionized gaseous phase downhole fluid, together with the measured volumes, pressure and/or temperature data collected by the sensor 1028 (FIGS. 2A and 2B) are used to compute the analyte concentration in the non-depressurized or pristine state downhole fluid as further detailed in FIG. 7.

Figure 5:
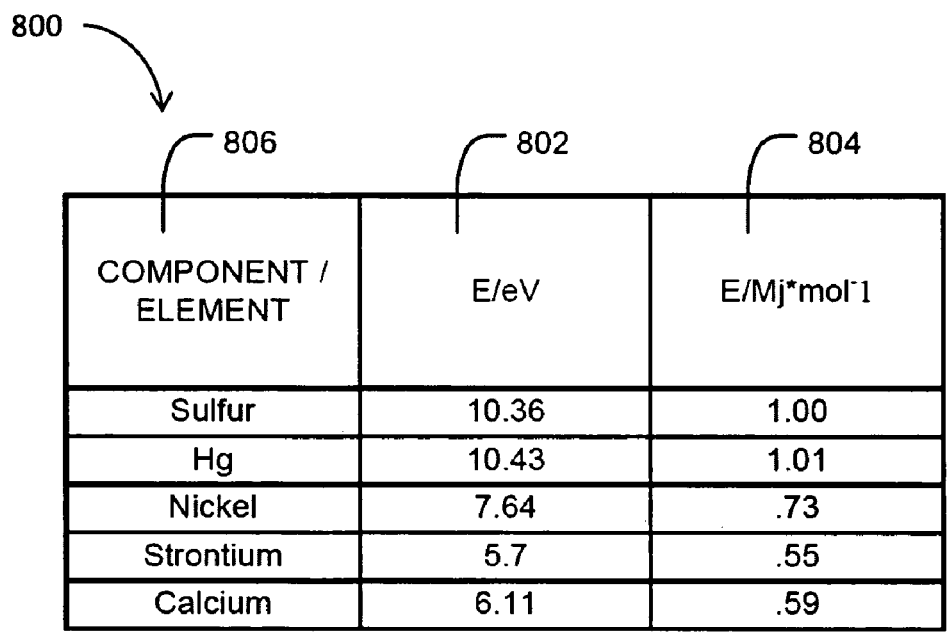
FIG. 5 depicts a table that includes a list of ionization energies for different components and elements.

The downhole control and data acquisition system 230 then determines whether it should analyze another formation fluid sample (block 520). For example, if the downhole tool 200 has drawn another formation fluid sample and the downhole control and data acquisition system 230 has not received an instruction or command to stop analyzing fluid, the downhole control and data acquisition system 230 may determine that it should analyze another fluid sample (block 520). Otherwise, the example process of FIG. 5 is ended.

FIG. 4 is a flow diagram depicting an example method 1100 that may be used to perform formation fluid samples depressurization using, for example, the example apparatus 1000 of FIGS. 2A and 2B. Initially, a sample of the downhole fluid flows through the flowline 1002. The downhole fluid is preferably extracted in a way that preserves its pristine state in the formation or in the wellbore (e.g. using single phase sampling techniques known in the art). Then the first valve 1008 and the second valve 1010, which were in an open position, are actuated to a closed position (block 1104), for example when sufficiently clean fluid is captured in the flowline 1002 between the first and second valves 1008 and 1010 (block 1102).

The motor 1014 then moves the piston 1012 toward the depressurized position, which expands the volume of the sample (block 1106). As the piston 1012 moves toward the depressurized position, the sensor 1028 measures the pressure and/or the temperature of the sample (block 1108). Additionally, as the piston 1012 moves, after the piston 1012 has reached a predetermined position or when a pressure of the formation fluid is reduced to a predetermined pressure, the phase of the sample is monitored by the sensor 1028 (block 1110). Specifically, data points of sample pressure versus volume of the depressurizing chamber below the piston 1012 are collected and analyzed to determine the bubble point pressure and its corresponding volume of the captured sample. Indeed, fluids are characterized by a low compressibility and therefore large pressure variations as the volume of the depressurizing chamber below the piston 1012 increases. In contrast, when gas bubble form in the sample, the compressibility of the fluid and gaseous phase increases noticeably. Thus, the volume of the depressurizing chamber below the piston 1012 corresponding to the apparition of a gaseous phase in the sample may be detected from the data points of sample pressure versus volume, as known in the art. Additionally or alternatively, the phase(s) of the sample and their corresponding volumes may be monitored using the phase detector 1025. Specifically, the volume of a phase of the sample may alternatively be determined by utilizing the sample phase detector 1025 to determine the volume or the level at which a portion of the sample that is in a liquid phase is positioned within the depressurizing chamber 1004.

If it is determined that only one phase is present in the fluid sample, the volume of the sample is expanded as discussed in connection with block 1106. However, if it is determined that more than one phase is present in the fluid (block 1112), the volume of the liquid phase (e.g., a non-measured or non-ionized phase) of the sample is determined and an estimate of the gaseous phase is determined based on the total volume of the depressurizing chamber below the piston 1012 and the determined volume of the liquid phase (block 1114). Conversely, the volume of the gas phase (e.g., a measured or ionized phase) of the sample may alternatively be determined and an estimate of the liquid phase determined based on the total volume of the depressurizing chamber below the piston 1012 and the determined volume of the liquid phase (block 1114).

FIG. 5 illustrates a table 800 that includes a list of ionization energies for a plurality of different components or elements. The table 800 includes an energy in electron volt (E in units of eV) column 802 and an energy of mega Joule per mol (E in units of MJ·mol$^{-1}$) column 804. Additionally, the table 800 includes a component or element column 806. The entries in the columns 802 and 804 adjacent the component or element column 806 are associated with the ionization energy that are needed to ionize and/or decompose the components or elements (e.g., sulfur, mercury, nickel, strontium, calcium).

For a component or element listed in column 806 and being analyzed, the downhole control and data acquisition system 230 or a surface system may be configured to select an ionization duration based its corresponding data of column 804. The ionization duration is the amount of time for which the formation fluid sample is to be exposed to, for example, an electrical field or charge, photons, etc. In addition, the downhole control and data acquisition system 230 or a surface system can select an energy level and/or wavelength size to use for the ionizing source (e.g. the ionizer 300 of FIG. 2A) based on data listed in column 802. Alternatively, the energy level and/or wavelength size may be used to identify a component or element listed in column 806 by comparing the energy level and/or wavelength size of a measured light (e.g. measured by the spectrometer 420 and/or 402' of FIG. 2B) to the data listed in column 802.

Turning to FIG. 6, the example reference database 234 may be configured or structured to store data generated using any suitable fluid analysis technique including the fluid analysis techniques described herein. In some example implementations, the reference measurement data stored in the reference database 234 may be generated using laboratory or uphole fluid analyses of fluid samples known to have particular fluid compositions (e.g., fluid samples known to have particular atoms and/or molecules and known concentrations of those atoms and/or molecules). Specifically, the reference database 234 may store measured light intensities observed at particular frequencies for known species and/or elements describing different fluid components or a concentration of analyte(s). Alternatively, the reference database 234 may store measured resistances of ionized samples of known species and/or elements after ionization at particular frequencies. In some examples, the reference database 234 may store characteristics of known species held within containers having known temperatures, and/or pressures.

In the illustrated example of FIG. 6, the reference database 234 includes an atom/molecule identifier column 702 and reference parameter measurement values columns 704. The atom/molecule identifier column 702 may be used to store names or identifiers of atoms and/or molecules that may be found in formation fluid samples. The reference parameter measurement values columns 704 are used to store reference measurement values of reference formation fluids known to have particular components (e.g., particular atoms or molecules) and concentrations of those components. As described above, the reference measurement values stored in the reference parameter measurement values columns 704 may be measured in a laboratory environment or some other uphole environment using any suitable fluid analysis technique including the fluid analysis techniques described herein. In the illustrated example, the reference parameter measurement values columns 704 include an analyte concentration column 710 to store the known concentrations of those atoms and/or molecules in reference fluid samples listed in column 702. The reference parameter measurement values columns 704 also include a sensor reading column 714 to store the parameter values measured by the sensor 219 after or during ionization of the reference fluid samples in a controlled environment.

While the reference database of FIG. 6 is depicted as a calibration table, the reference database 234 may alternatively be implemented using a neural network that has been trained to reproduce the known concentrations of those atoms and/or molecules in reference fluid samples listed in column 702 as a function of the parameter values measured by the sensor 219 after or during ionization of the reference fluid samples in a controlled environment. Further, the reference database of FIG. 6 may also be implement using curve fitting techniques, such as radial basis functions, to reproduce the calibration table.

FIG. 7 is a flow diagram of an example method 600 that may be used to determine analyte concentration in a fluid sample. Specifically, the volumes of liquid and gaseous phases of the fluid sample after depressurization are determined, using for example the method described in FIG. 6 (block 610). When the sampled downhole fluid is a formation gas, only the volume of gaseous is determined. Further, the pressure and the temperature of the sample may also be measured by the sensor 1028 (block 615). Still further, composition data may be determined with the fluid measurement unit 220 (block 620). For example, composition data such as the molar weight of methane (C1), the molar weight of carbon dioxide (CO2), the molar weight of water, the molar weight of alkanes having six or more carbon atoms in the molecule (C6+) may be determined using visible and near infra red spectroscopy techniques known in the art. These composition data may be used to identify a sample type (water, gas, gas retrograde condensate, light oil, medium oil, heavy oil, etc . . . ) of the sample downhole fluid.

The detected and/or measured values by the sensor 219 (FIG. 1) during or after ionization of at least a portion of the depressurized sample (e.g. the gaseous phase) are then compared to a reference database such as the reference database 234 (FIG. 6) that may contain a plurality of known measurements and/or data that may have been obtained from subterranean formations that have similar conditions. By comparing the detected property of the ionized sample (e.g. the ionized gaseous phase), with known reference parameters, the concentration in one or more analyte(s) in the portion of the depressurized sample (e.g. the gaseous phase) may be determined (block 625).

Additionally, the concentration in one or more analyte(s) in a liquid portion of the sample that has not been ionized is determined (block 630). For example, the thermodynamics equilibrium between the analyte in the gaseous phase and the analyte still in solution in the liquid phase can be used to compute the concentration in one or more analyte(s) in a liquid phase of the sample. Specifically, the ratio of the analyte concentration in the gaseous phase (e.g. its partial pressure) against the analyte concentration in the liquid phase may be a function of the sample fluid pressure and temperature measured at block 615, and the sample fluid type and/or sample fluid composition data measured at block 620. Thus, a relationship derived for example empirically and representative of the thermodynamics equilibrium may be used to compute the concentration in one or more analyte(s) in a liquid portion of the sample from the concentration in the one or more analyte(s) in the gaseous phase of the depressurized sample derived at clock 625, and auxiliary measurements derived at block 615 and 620. In some implementations, the relationship may be implemented with a calibration table obtained similarly to the table of FIG. 6.

Also, the concentration of the analyte in the downhole fluid sample prior to depressurization may be computed (block 635). Specifically, the persons skilled in the art will appreciate that the concentration of the analyte in the downhole fluid sample prior to depressurization may be obtained from the gaseous and liquid volumes of the sample determined at block 610, as well as the concentration of analytes determined at block 630 and 635.

While a particular method has been described in FIG. 7, it will be appreciated that other method may alternatively be used. For example, theoretical or empirical data may be used to determine a pressure level, that may be function of the temperature and the fluid type, at which the concentration of a particular analyte in the liquid phase is essentially negligible. Thus, by insuring a depressurization of the fluid sample at least below this threshold value, the operation associated with the block 630 are reduced to assume a zero concentration of the analyte in the liquid phase provided a criterion based on pressure, and optionally temperature and fluid type, is met.

Figure 8A:
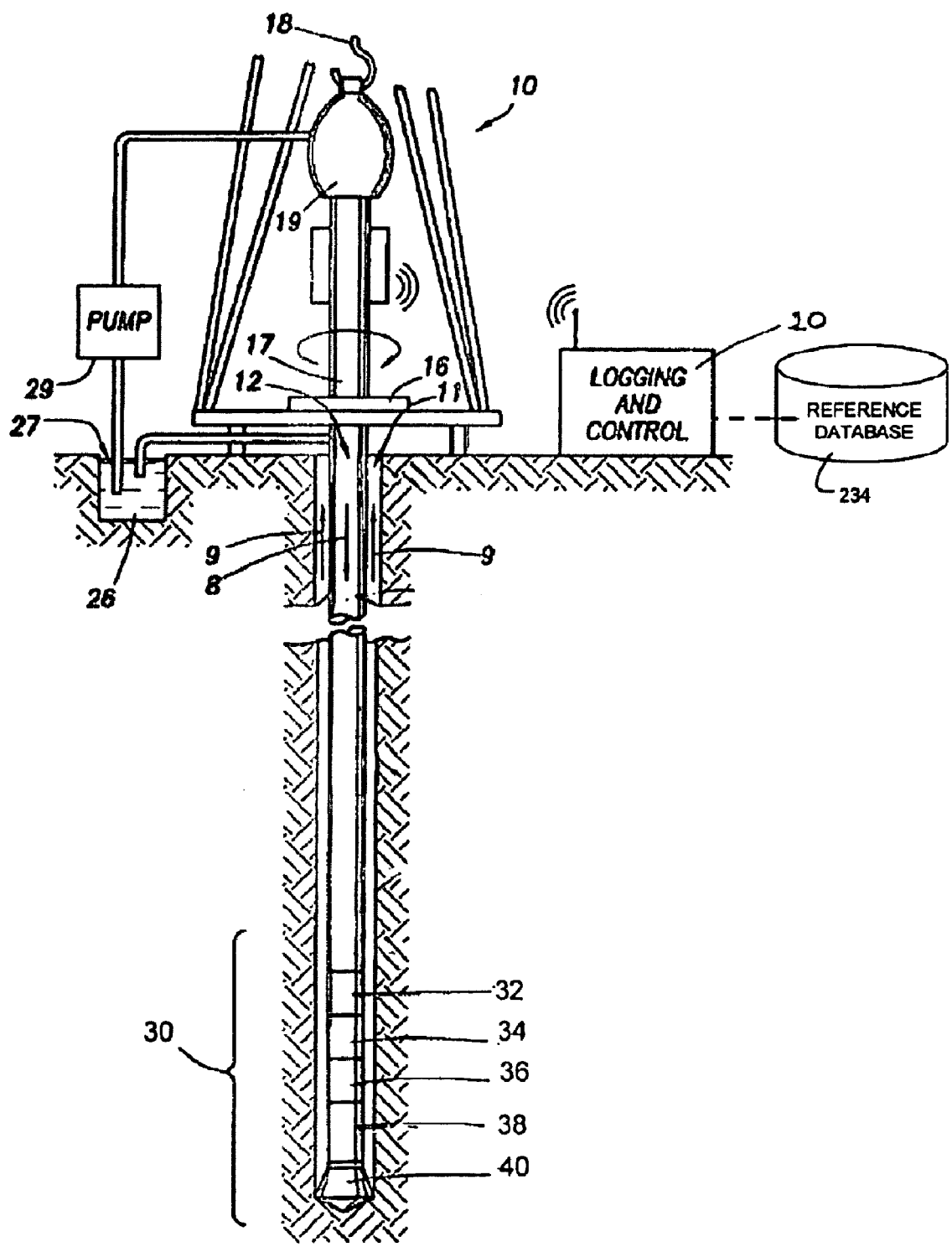
FIG. 8A depicts an example wellsite system in which the example downhole tool described herein can be employed.

FIG. 8A illustrates a wellsite system in which the example implementations can be employed. The wellsite can be onshore or offshore. In this example system, a borehole 11 is formed in subsurface formations by rotary drilling in a manner that is well known. Some example implementations can also use directional drilling.

A drill string 12 is suspended within the borehole 11 and has a bottom hole assembly 30 that includes a drill bit 40 at its lower end. The wellsite system includes a platform and derrick assembly 10 positioned over the borehole 11. The assembly 10 includes a rotary table 16, a kelly 17, a hook 18 and a rotary swivel 19. The drill string 12 is rotated by the rotary table 16, energized by means not shown, which engages the kelly 17 at the upper end of the drill string 12. The drill string 12 is suspended from the hook 18, which is attached to a traveling block (also not shown), through the kelly 17 and the rotary swivel 19, which permits rotation of the drill string 12 relative to the hook 18. As is well known, a top drive system could alternatively be used.

In the illustrated example implementation, the wellsite system further includes drilling fluid or mud 26 stored in a pit 27 formed at the well site. A pump 29 delivers the drilling fluid 26 to the interior of the drill string 12 via a port in the rotary swivel 19, causing the drilling fluid 26 to flow downwardly through the drill string 12 as indicated by a directional arrow 8. The drilling fluid 26 exits the drill string 12 via ports in the drill bit 40, and then circulates upwardly through the annulus region between the outside of the drill string 12 and the wall of the borehole 11, as indicated by directional arrows 9. In this well-known manner, the drilling fluid 26 lubricates the drill bit 40 and carries formation cuttings to the surface as it is returned to the pit 27 for recirculation.

The bottom hole assembly (BHA) 30 of the illustrated example implementation includes a logging-while-drilling (LWD) module 32, a measuring-while-drilling (MWD) module 34, a roto-steerable system and motor 38, and drill bit 40. In the illustrated example, the bottom assembly 30 is communicatively coupled to a logging and control unit 20. The logging and control unit 20 may be configured to receive data from and control the operation of the logging-while-drilling (LWD) module 32, the measuring-while-drilling (MWD) module 34, and the roto-steerable system and motor 38. In particular, the logging and control unit 20 may be configured to control the trajectory of the borehole 11 based on data collected from one or more component of the BHA 30, as well as a reference data base (not shown) coupled to the logging and control unit 20. While the logging and control unit 20 is depicted on the well site in FIG. 8A, at least a portion of the logging and control unit 20 may alternatively be provided at a remote location.

The LWD module 32 is housed in a special type of drill collar, as is known in the art, and can contain one or a plurality of known types of logging tools. It will also be understood that more than one LWD and/or MWD module can be employed (e.g., as represented at 36). (References, throughout the following description, to a module at the position of 32 can alternatively mean a module at the position of 36 as well.) The LWD module 32 includes capabilities for measuring, processing, and storing information, as well as for communicating with the MWD module 34. In the illustrated example implementation, the LWD module 32 includes a sampling device (not shown).

The MWD module 34 is also housed in a special type of drill collar, as is known in the art, and can contain one or more devices for measuring characteristics of the drill string 12 and the drill bit 40. The MWD module 34 further includes an apparatus (not shown) for generating electrical power to the downhole system. This may typically include a mud turbine generator powered by the flow of the drilling fluid 26, it being understood that other power and/or battery systems may be employed. In the illustrated example implementation, the MWD module 34 includes one or more of the following types of measuring devices: a weight-on-bit measuring device, a torque measuring device, a vibration measuring device, a shock measuring device, a stick slip measuring device, a direction measuring device, and an inclination measuring device. The MWD module 34 also includes capabilities for processing, and storing information signals from the LWD module 32 and 36, as well as for communicating with the surface equipment.

Figure 8B:
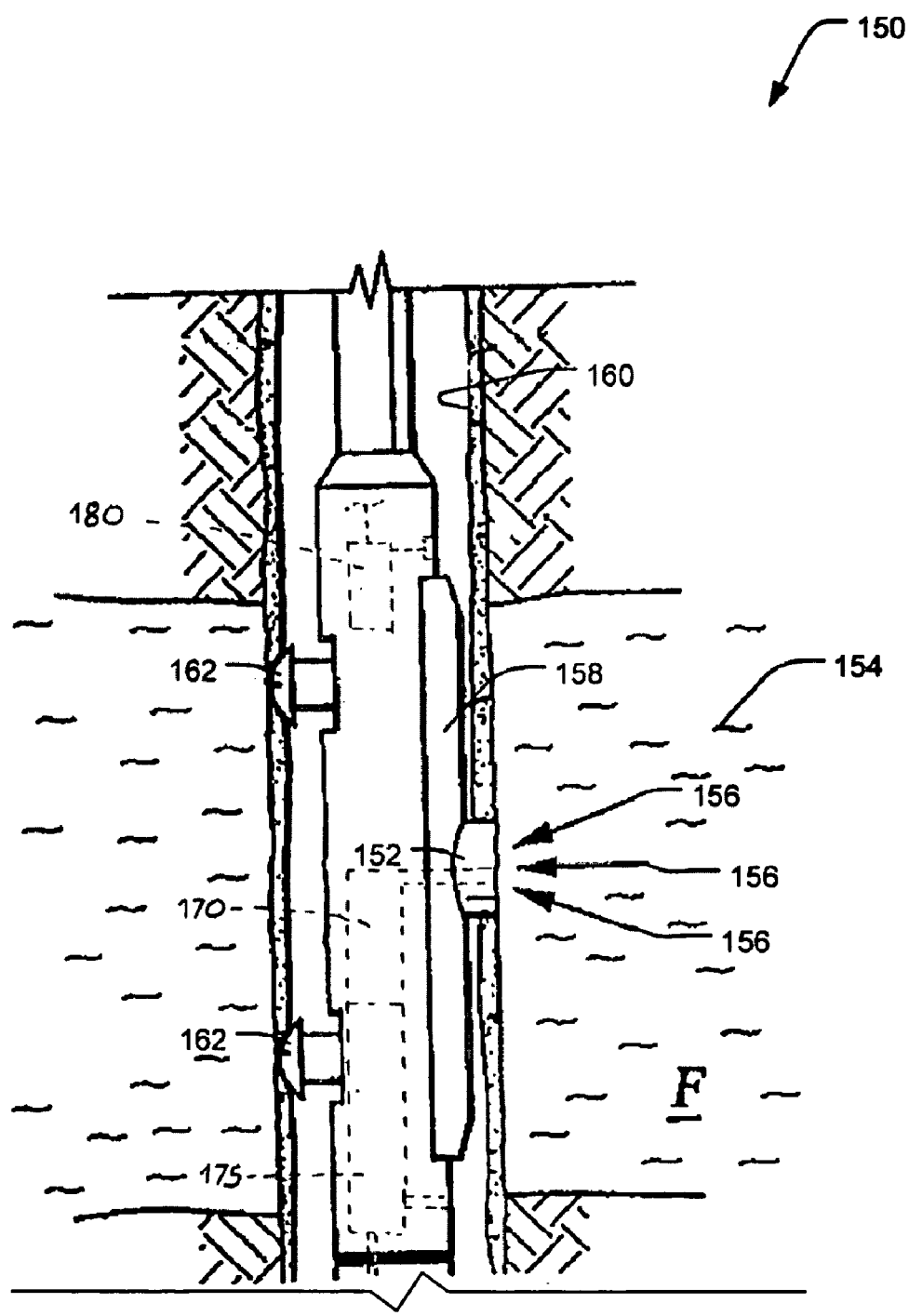
FIG. 8B depicts a block diagram of a logging device shown in FIG. 7A.

FIG. 8B is a simplified diagram of a sampling-while-drilling logging device 150 (LWD tool 150), and may be used to implement the LWD module 36 of FIG. 8A. In the illustrated example, the LWD tool 150 is of a type described in U.S. Pat. No. 7,114,562, which is assigned to the assignee of the present patent and incorporated herein by reference in its entirety. However, other types of pressure measuring LWD tools can be used to implement the LWD tool 150 or part of an LWD tool. A probe 152 may extend from a stabilizer blade 158 of the LWD tool 150 to engage a bore wall 160. The stabilizer blade 158 includes one or more blades that engage the bore wall 160. The LWD tool 150 may be provided with a plurality of backup pistons 162 to assist in applying a force to push and/or move the LWD tool 150 and/or the probe 152 against the bore wall 160.

The probe 152 is configured to selectively seal off or isolate selected portions of the wall of the wellbore 160 to fluidly couple to the adjacent formation F and draw fluid samples from the formation F into the LWD tool 150 in a direction generally indicated by arrows 156, for example by using a pump 175 (for example similar to the pump 208 of FIG. 1). Once the probe 152 fluidly couple to the adjacent formation F, various measurements may be conducted on the sample such as, for example, a pretest parameter or a pressure parameter may be measured. The LWD module 36 also includes a fluid analysis module 170 through which the obtained fluid samples flow. The fluid may thereafter be expelled through a port (not shown) or it may be sent to one or more fluid collecting chambers (not shown), which may receive and retain the formation fluid for subsequent testing at the surface or a testing facility. In the illustrated example, a downhole control system 180 is configured to control the operations of the LWD module 36 to draw fluid samples from the formation F and to control the fluid analysis module 170 to measure the fluid samples. The fluid analysis module 170 may be configured to generate the measurement data as described therein, and in particular in connection with the sensor 219 and optionally the fluid measurement unit 220 of FIG. 1. In some example implementations, the downhole control system 180 may be configured to analyze the measurement data of the fluid samples as described herein. The downhole control system 180 capabilities for processing, and storing information, in particular for subsequent retrieval at the surface and/or for real time communication with the surface equipment.

Figure 9:
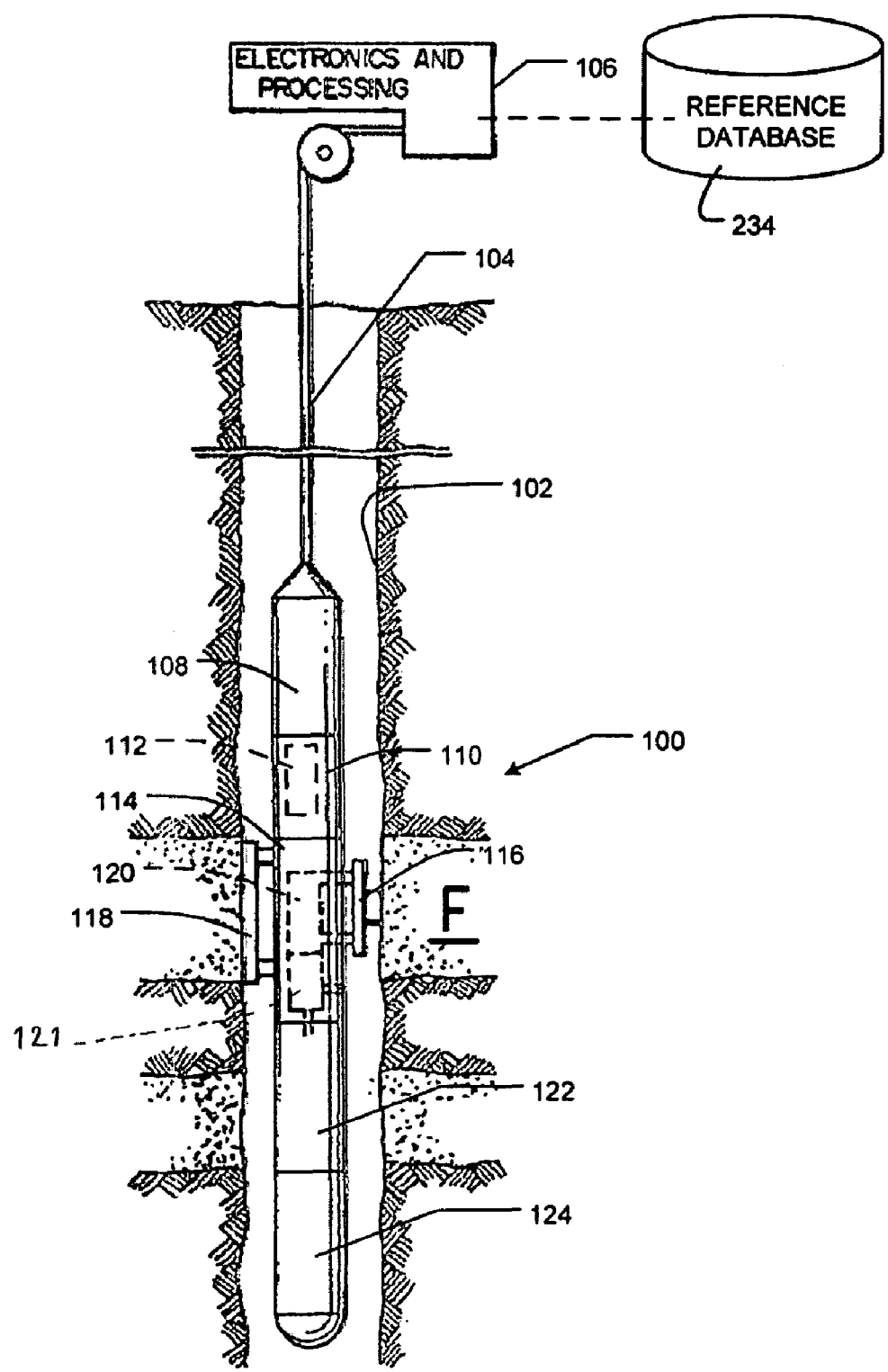
FIG. 9 depicts another example wellsite system in which the example downhole tool described herein can be employed.

Turning to FIG. 9, an example wireline tool 100 that may be used to extract and analyze formation fluid samples is suspended in a wellbore 102 from the lower end of a multiconductor cable 104 that is spooled on a winch (not shown) at the Earth's surface. At the surface, the cable 104 is communicatively coupled to an electrical control and data acquisition system 106. The wireline tool 100 includes an elongated body 108 that includes a module 110 having a downhole control system 112 communicatively coupled to the electrical control and data acquisition system 106 and configured to control extraction of formation fluid from the formation F and measurements performed on the extracted fluid, as well as store and/or communicate the measurement data to the surface for subsequent analysis at the surface.

The wireline tool 100 also includes a formation tester 114 having a selectively extendable fluid admitting assembly 116 and a selectively extendable tool anchoring member 118 that are respectively arranged on opposite sides of the body 108. The fluid admitting assembly 116 is configured to selectively seal off or isolate selected portions of the wall of the wellbore 102 to fluidly couple to the adjacent formation F and draw fluid samples from the formation F using for example a pump 121 (for example similar to the pump 208 of FIG. 1). The formation tester 114 also includes a fluid analysis module 120 through which the obtained fluid samples flow. The fluid may thereafter be expelled through a port (not shown) or it may be sent to one or more fluid collecting chambers 122 and 124 (for example similar to the fluid store 226 of FIG. 1), which may receive and retain the formation fluid for subsequent testing at the surface or a testing facility. In the illustrated example, the electrical control and data acquisition system 106 and/or the downhole control system 112 are configured to control the fluid admitting assembly 116 to draw fluid samples from the formation F and to control the fluid analysis module 120 to measure the fluid samples. The fluid analysis module 120 may be configured to generate the measurement data as described therein, and in particular in connection with the sensor 219 and optionally the fluid measurement unit 220 of FIG. 1. In some example implementations, the downhole control system 112 may be configured to analyze the measurement data of the fluid samples as described herein, for example in connection with the downhole control and data acquisition 230 of FIG. 1. In other example implementations, the fluid analysis module 120 may be configured to generate the measurement data and subsequently communicate the measurement data to the surface for subsequent analysis at the surface via the downhole control system 112. In this case, the electrical control and data acquisition system 106 may be configured to analyze the measurement data of the fluid samples as described herein. Although the downhole control system 112 is shown as being implemented separate from the formation tester 114, in some example implementations, the downhole control system 112 may be implemented in the formation tester 114.

While the foregoing examples describe example sampling tools as being implemented as wireline and drillstring devices, any other manner of deploying tools in boreholes could be used instead. For example, coiled tubing may be used to implement the example methods and apparatus described herein to achieve similar or identical results. Further, while the examples described herein are depicted in use with an uncased borehole, the example methods and apparatus described herein could also be employed in cased boreholes.

Although certain methods, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

What is claimed is:

1. A method of analyzing a downhole fluid, the method comprising:
   conveying a testing tool in a wellbore, the testing tool having an inlet, a depressurizer, an ionizer, and a fluid measurement unit;
   obtaining a sample of the downhole fluid via the inlet;
   depressurizing at least a portion of the sample via the depressurizer;
   measuring a depressurizing pressure of the at least portion of the sample;
   ionizing the at least portion of the sample via the ionizer;
   performing an analysis of the ionized portion of the sample; and
   determining a parameter of the downhole fluid from the measured depressurizing pressure and the analysis of the ionized portion of the sample.

2. The method of claim 1 wherein ionizing the at least portion of the sample comprises exposing the at least the portion of the sample to an ionizing energy generated using photons, and wherein performing an analysis of the ionized portion of the sample comprises performing at least one resistivity measurement on the ionized portion of the sample.

3. The method of claim 1 wherein performing an analysis of the ionized portion of the sample comprises identifying an atom associated with a wavelength of at least one of a photon emission and a photon absorption.

4. The method of claim 1 wherein ionizing the at least portion of the sample comprises exposing the at least the portion of the sample to an ionizing energy generated using electrons, and wherein performing an analysis of the ionized portion of the sample comprises performing at least one optical measurement on the ionized portion of the sample.

5. The method of claim 4 further comprising measuring a light intensity associated with the wavelength of the photon emission, determining a concentration of the atom based on the light intensity, and using the concentration of the atom to determine a parameter of the downhole fluid.

6. The method of claim 5 wherein the parameter of the downhole fluid is indicative of the concentration of the molecule present in the downhole fluid.

7. The method of claim 6 wherein the concentration of the molecule present is hydrogen sulfide.

8. The method of claim 1 wherein depressurizing at least a portion of the sample comprises extracting a gaseous phase from the fluid sample.

9. The method of claim 8 wherein ionizing the at least portion of the sample comprises ionizing the gaseous phase from the fluid sample.

10. The method of claim 9 wherein the parameter of the downhole fluid is at least one of a concentration of a molecule in the gaseous phase and a concentration of a molecule present in sample prior to depressurization.

11. The method of claim 1 further comprising measuring a volume indicative of the volume of the at least portion of the sample ionized via the ionizer, and wherein determining a parameter of the downhole fluid is further based on the measured volume.

12. The method of claim 1 wherein the parameter of the downhole fluid is the concentration of a molecule present in the downhole fluid.

13. The method of claim 1 wherein the parameter of the downhole fluid is associated with composition data of the downhole fluid.

14. The method of claim 1 wherein ionizing the at least portion of the sample comprises changing the at least the portion of the sample to a plasma.

15. The method of claim 1 wherein the parameter of the downhole fluid is associated with a concentration of at least one of sulfur, radon, nitrogen, oxygen, helium, methane, ethane, and propane.

16. The method of claim 1 wherein the downhole fluid is at least one of a wellbore fluid or a fluid extracted from a subsurface formation.

17. The method of claim 1 wherein conveying the testing tool in the wellbore comprises lowering the testing tool via one a wireline cable and a drill string.

18. An apparatus to analyze a downhole fluid, comprising:
   a testing tool adapted for conveyance in a wellbore, the testing tool comprising an inlet for obtaining a sample of the downhole fluid, a depressurizer to depressurize at least a portion of the sample, an ionizer to ionize the at least the portion of the sample, and a fluid measurement unit to measure a characteristic of the ionized portion of the sample; and
   a processing unit to determine a parameter of the downhole fluid based on the characteristic of the ionized portion of the sample and a depressurizing pressure of the at least the portion of the sample.

19. The apparatus of claim 18 wherein the ionizer comprises one of a high voltage source, a photon source, or a lightwave source.

20. The apparatus of claim 18 wherein the fluid measurement unit is at least one of a spectrometer or a resistivity measurement unit.

21. The apparatus of claim 18 wherein the fluid measurement unit is to measure a photon emission from the at least the portion of the sample, and wherein the processing unit is to identify an atom associated with a wavelength of the photo emission and use the identified atom to determine the parameter of the downhole fluid.

22. The apparatus of claim 21 wherein the fluid measurement unit is to measure a light intensity associated with the wavelength of the photon emission, and wherein the processing unit is to determine a concentration of the atom based on the light intensity and use the concentration of the atom to determine the parameter of the downhole fluid.

23. The apparatus of claim 18 wherein the ionizer is to bombard the portion of the sample with photons having a wavelength to excite a type of atom, wherein the fluid measurement unit is to measure a resistivity of the ionized sample while being bombarded with the photons, and wherein the processing unit is to determine a concentration of the type of atom based on the resistivity to determine the parameter of the downhole fluid.

24. The apparatus of claim 18 further comprising a volume measuring device for measuring a volume indicative of the volume of the at least portion of the sample ionized via the ionizer.

25. The apparatus of claim 18 wherein the parameter of the downhole fluid is associated with composition data of the downhole fluid.

26. The apparatus of claim 25 wherein the parameter of the downhole fluid is a concentration of a molecule present in the downhole fluid.

27. The apparatus of claim 18 wherein the parameter of the downhole fluid is associated with a concentration of at least one of mercury, nickel, vanadium, sulfur, radon, polonium, barium, strontium, nitrogen, calcium, oxygen, helium, methane, ethane, and propane.

28. The apparatus of claim 18 wherein the downhole fluid is at least one of a wellbore fluid or a fluid extracted from a subsurface formation.

29. The apparatus of claim 18 wherein the testing tool is conveyed in the wellbore via a wireline cable.

30. The apparatus of claim 18 wherein the testing tool is conveyed in the wellbore via a drill string.

* * * * *